(12) United States Patent
Ostler et al.

(10) Patent No.: US 11,062,622 B2
(45) Date of Patent: *Jul. 13, 2021

(54) REWARD CLOCK

(71) Applicants: Derek Ostler, Wentzville, MO (US); Ashley Ostler, Wentzville, MO (US)

(72) Inventors: Derek Ostler, Wentzville, MO (US); Ashley Ostler, Wentzville, MO (US)

(73) Assignee: HAPPY TYKES, INC., Wentzville, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/994,035

(22) Filed: Aug. 14, 2020

(65) Prior Publication Data
US 2020/0372829 A1 Nov. 26, 2020

Related U.S. Application Data

(63) Continuation-in-part of application No. 16/595,244, filed on Oct. 7, 2019, now Pat. No. 10,761,486, which
(Continued)

(51) Int. Cl.
*G09B 19/12* (2006.01)
*A61M 21/02* (2006.01)
(Continued)

(52) U.S. Cl.
CPC ............. *G09B 19/12* (2013.01); *A61M 21/02* (2013.01); *G04B 45/0069* (2013.01); *A61M 2021/0027* (2013.01)

(58) Field of Classification Search
CPC .... G04G 17/08; G04G 9/0017; G04G 9/0064; G04G 13/021; G04G 21/08; G04C 17/00
(Continued)

(56) References Cited

U.S. PATENT DOCUMENTS 3,985,104 A 10/1976 Klemer
4,216,594 A 8/1980 Farley et al.
(Continued)

OTHER PUBLICATIONS

"Gro Clock from the Gro Company, makers of the Grobag baby sleeping bad", Youtube, published Mar. 18, 2009, Accessed Feb. 4, 2020 via https://www.youtube.com/watch?v=6m4CgEEeQHk.
(Continued)

*Primary Examiner* — Edwin A. Leon
(74) *Attorney, Agent, or Firm* — Workman Nydegger

(57) ABSTRACT

The present invention is directed to devices that may be used to help young children stay in bed or their room until it is time to get up. The device may be configured as a clock. The clock may be programmable to have a duration of a nap time, or a time when the child is able to get up. A visual countdown timer may be provided with the device (e.g., on the clock face), which may include a graphical representation of the remaining fraction of time before "get up" time. The visual countdown timer may not include number indicia, but rather includes a graphic (e.g., ring extending about the perimeter of the clock face), which gradually diminishes as the predetermined "get up" time is approached. A reward drawer may also be provided, which automatically unlocks at the "get up" time, and provides the child with a prize.

20 Claims, 12 Drawing Sheets

Related U.S. Application Data is a continuation-in-part of application No. 16/261,045, filed on Jan. 29, 2019, now Pat. No. 10,437,200.

(60) Provisional application No. 62/798,123, filed on Jan. 29, 2019.

(51) Int. Cl.
*G04B 45/00* (2006.01)
*A61M 21/00* (2006.01)

(58) Field of Classification Search
USPC .............................. 368/276, 10, 72–73, 250
See application file for complete search history.

(56) References Cited

U.S. PATENT DOCUMENTS

| | | | | |
|---|---|---|---|---|
| 4,531,841 | A * | 7/1985 | Puff | G04B 45/0061 368/228 |
| 4,730,284 | A | 3/1988 | Adams | |
| 5,159,581 | A | 10/1992 | Agans | |
| D335,939 | S | 5/1993 | Cooper | |
| 5,283,769 | A * | 2/1994 | Renton | G04B 25/005 368/250 |
| 5,288,233 | A | 2/1994 | Green | |
| 5,684,758 | A | 11/1997 | Gray et al. | |
| 5,752,235 | A | 5/1998 | Kehr et al. | |
| 6,116,775 | A | 9/2000 | Masateru | |
| 6,843,158 | B2 | 1/2005 | Garcia et al. | |
| 6,894,434 | B1 | 5/2005 | Kosoff | |
| 7,051,675 | B1 | 5/2006 | Mayer et al. | |
| 7,209,044 | B2 | 4/2007 | Reustle | |
| 7,453,365 | B2 | 11/2008 | Reustle | |
| 8,169,859 | B1 | 5/2012 | Sheehan | |
| 8,963,707 | B2 | 2/2015 | Bevel | |
| 9,234,668 | B2 | 1/2016 | Fadell et al. | |
| 9,513,642 | B2 | 12/2016 | Rogers et al. | |
| 9,527,001 | B2 | 12/2016 | Richardson et al. | |
| 9,568,370 | B2 | 2/2017 | Fadell et al. | |
| D797,575 | S | 9/2017 | Lai et al. | |
| 9,942,611 | B2 | 4/2018 | Kageyama | |
| 9,967,728 | B2 | 5/2018 | Logue et al. | |
| 10,437,200 | B1 | 10/2019 | Ostler | |
| 10,761,486 | B2 * | 9/2020 | Ostler | G04F 1/005 |
| 2003/0126977 | A1 | 7/2003 | Garcia et al. | |
| 2005/0275544 | A1 | 12/2005 | Reustle | |
| 2005/0284414 | A1 | 12/2005 | Garcia et al. | |
| 2007/0217290 | A1 | 9/2007 | Rock | |
| 2008/0030349 | A1 | 2/2008 | Reustle | |
| 2008/0192580 | A1 | 8/2008 | Larian | |
| 2009/0108034 | A1 | 4/2009 | Bechyne et al. | |
| 2010/0203490 | A1 | 8/2010 | Hocherman | |
| 2010/0301074 | A1 | 12/2010 | Koesterich | |
| 2013/0256256 | A1 | 10/2013 | Krippendorf et al. | |
| 2013/0338839 | A1 | 12/2013 | Rogers et al. | |
| 2014/0295388 | A1 | 10/2014 | Izak et al. | |
| 2014/0295389 | A1 | 10/2014 | Izak et al. | |
| 2015/0378320 | A1 | 12/2015 | Knight et al. | |
| 2017/0146261 | A1 | 5/2017 | Rogers et al. | |
| 2017/0180808 | A1 | 6/2017 | Kageyama | |
| 2020/0241478 | A1 | 7/2020 | Ostler | |
| 2020/0372829 | A1 | 11/2020 | Ostler | |

OTHER PUBLICATIONS

LittleHippo Mella on Amazon Q&A, Accessed Feb. 21, 2019 URL: https://www.amazon.com/ask/questions/asin/B078Z5CXTX/ref=ask_mdp_dpmw_ql_hza?isAnswered=true.

LittleHippo Mella on Amazon, Accessed Feb. 21, 2019 URL: https://www.amazon.com/gp/product/B078Z5CXTX/ref=ask_ql_qh_dp_hza.

LittleHippo Mella Ready to Rise Children's Trainer, Alarm Clock, Night Light and Sleep Sounds Machine on Amazon Accessed Sep. 30, 2019 https://www.amazon.com/LittleHippo-Childrens-Trainer-Sounds-Machine/dp/B078Z5FHG9.

Littlehippo; Introducing Mella, Accessed Feb. 21, 2019 URL: https://www.littlehippo.com/.

Littlehippo; Story, Accessed Feb. 21, 2019 URL: https://www.littlehippo.com/pages/about-us.

Mella on Littlehippo; Accessed Jan. 18, 2019 URL: https://littlehippo.com/products/mella.

Mella: "All-In-One Clock to Keep Your Kid in Bed Longer" Kickstarter, Accessed Feb. 21, 2019 URL: https://www.kickstarter.com/projects/littlehippo/mella-all-in-one-clock-to-keep-your-kid-in-bed-lon.

Pali: "The sleep trainer that has a countdown timer young kids can SEE and UNDERSTAND", Accessed Feb. 4, 2020 via www.happytykes.com.

U.S. Appl. No. 16/261,045, Apr. 2, 2019, Office Action.
U.S. Appl. No. 16/261,045, Jun. 7, 2019, Notice of Allowance.
U.S. Appl. No. 16/595,244, Jun. 15, 2020, Office Action.
U.S. Appl. No. 16/595,244, Jul. 24, 2020, Notice of Allowance.
Office Action received for U.S. Appl. No. 16/595,244, dated Jun. 15, 2020.
U.S. Appl. No. 15/595,244, filed Oct. 7, 2019 by Ostler.

* cited by examiner

REWARD CLOCK

CROSS-REFERENCE TO RELATED APPLICATION

This application is a continuation-in-part under 35 U.S.C. 120 of U.S. application Ser. No. 16/595,244, entitled REWARD CLOCK, filed Oct. 7, 2019, which is a continuation-in-part under 35 U.S.C. 120 of U.S. application Ser. No. 16/261,045, entitled REWARD CLOCK, filed Jan. 29, 2019, which is now U.S. Pat. No. 10,437,200, which claims the benefit under 35 U.S.C. 119(e) of U.S. Provisional Patent Application No. 62/798,123, filed Jan. 29, 2019, each of which is herein incorporated by reference in its entirety.

BACKGROUND

Unless otherwise indicated herein, the materials described in this section are not necessarily prior art to the claims in this application and are not admitted to be prior art by inclusion in this section.

1. Field of the Invention

The present invention relates generally to clocks specifically configured for particular use by children. More specifically, the present invention relates to a clock that provides a reward to a child after a certain amount of time has passed.

2. Description of Related Art

While various alarm clocks and other clocks are available in the art, there remains a need for clocks specifically configured for use with young children who may have difficulty remaining in bed at bed time, for the entire sleep time that would be desired by a parent.

BRIEF SUMMARY OF THE INVENTION

The present invention involves a "Pali" clock designed to help parents sleep longer by helping children know when it is acceptable to get out of bed. The clock may have any variety of special features, including one or more of a visual (e.g., circular) timer, a reward function, a nightlight, a sound machine, and/or an alarm. A companion app (e.g., for use with a smartphone or the like) may allow parents to easily customize various features of the clock.

The idea of the Pali clock is that, at a set time, the visual (circle) timer will begin counting down. When the timer ends the clock will light up and a reward drawer will unlock. A child using the clock can then get a reward for waiting in their room until the designated time and may then go find their parents. The Pali clock may include a mechanism to ensure that the reward drawer is not unlocked, if the child leaves their bed (or room) early. The Pali clock may be visually pleasing and simple to use. The exterior may be provided in any shape, examples of which are shown in the FIGS. The material used for the clock may be sufficiently transparent to allow a light to show through. For example, the clock may include an internal lamp that illuminates through the body of the clock, through a given material. Examples of such materials may include materials that are clear (transparent), translucent, thermochromic, or perforated. The clock may include a colored ring around the face of the clock that may be selectively removable so as to be interchangeable with a ring of a different color, pattern, indicia, images, or the like, so that each user can customize the appearance of their clock to suit their own tastes.

The clock may include a locking drawer that may selectively open and close. The locking drawer may not be accessible to be unlocked by the child, but only upon preset conditions as set by the parent or other adult user. The clock may provide buttons that may be hidden by a cover or panel. Such buttons may be functional to set an alarm, the time, the length of illumination for a night light, the length of time for a radio, sound machine, or other audio play to remain on, the sleep or wake time, the length for a nap time, the brightness of the screen, and/or a Reward or No Reward button. It will be apparent that various other controls may also be provided. These buttons can be positioned in 2 rows or otherwise arranged best for manufacturing, ergonomic appeal, or other factor.

Buttons on the exterior, such as on the ears of an animal shaped body of the clock, may turn off the alarm, begin nap time, or provide other functionality. For example, this may be accomplished by holding such a button for a predetermined time, such as 3 seconds, to begin nap time, or initiate other activity. In an embodiment, the other ear may include a button which may turn on or off the night light or adjust nightlight brightness. The clock may be touched multiple times (e.g., 3 or more times) to access a corresponding number (e.g., 3 or more) levels of brightness. A sound machine or radio incorporated in the clock may be turned on by pushing down a button associated with the ear for 3 seconds. In an embodiment, a power cord may be provided. Examples of such may include a micro USB cord, e.g., at least 5 feet long, normal power cord to be connected to a wall socket, or other type of power cord may be provided.

The clock is meant to be a child's nighttime pal that will "sleep" when they sleep and let them know when it is acceptable to wake up to play. In an embodiment, the face may be about 3.5 inches in diameter, although it will be appreciated that any size, shape or dimensions are possible. The clock face may have eyes and a mouth that can be set to "sleep" and wake up at a specific time. The clock face may include a plurality of visual "Z" indicia, indicating sleep time. When the countdown has begun, the clock face may still be "sleeping" but "ZZZ's" may go off once the countdown begins, or shortly thereafter (e.g., within 1 minute or the like).

The digital time may be displayed at all times, unless the countdown timer has been activated. When the countdown is active, the time remaining in such countdown may be shown in place of the time of day (HH:MM or MM:SS, depending on amount of time remaining).

By way of specific example, the digital time may show 10:00 AM as the time of day, or the timer may activate, at which time the digital time no longer shows, but the countdown timer may display a time remaining in the countdown, such as 43 minutes and 32 seconds left.

When the visual countdown timer is activated, a ring or other perimeter around the outside edge of the face may illuminate or otherwise appear. This ring or perimeter may initially surround the full perimeter of the clock face (e.g., 360°, as a full "ring"). As the countdown proceeds, the ring or other illuminated perimeter may progressively recede, corresponding to the fraction of time currently remaining in the countdown. For example, the original timer may be set to 1 hour long. When the timer is activated, the full 360° circle may be filled and illuminated. When the timer is down to 45 minutes, there may only be ¾ a circle, at 30 minutes ½ a circle, etc.

During daytime or wake time, the clock face may include a representation of the sun illuminated next to the time. During the set Sleep Time (i.e., when sleep time is active), a representation of the moon may be illuminated next to the time.

If selectively set by the app, during the daytime, the screen may change from a face (with representative facial features, such as eyes, nose, and/or mouth) to a face clock with minute and hour hands, with the digital time displayed below it. The Reward Function is a particularly advantageous aspect of the Pali clock. If a child waits until the designated time as set by the parent user, they can get a reward from the reward drawer that is included within the clock.

The drawer may be in the back of the clock. The drawer should be sturdy and easily slidable. The dimensions of the drawer may be as desired. By way of example, the drawer may be approximately 3 inches wide, 2 inches tall and 3 inches deep. Any of such dimensions could be varied by up to 1 inch, by up to 50%, or other amounts, depending on need.

The drawer advantageously may lock when a Reward/No Reward button on the clock is pushed. The drawer may unlock when the timer goes off UNLESS the reward/No Reward button has been pushed (locking the drawer, and overriding the unlocking that may otherwise occur). If it is the case that the Reward/No Reward button has been pushed by the adult user, e.g., after sleep time has started (e.g., because the child has gotten up during sleep or nap time), then the drawer may remain locked until the next time the timer ends, at which time another period for the child to earn a reward may begin. The drawer may advantageously lock and unlock silently, e.g., with no audible clicking, such that any change in the lock status is not heard by the child as caused by the locking mechanism itself.

When the timer goes off, the clock may light up at an intermediate "Medium" brightness (this default may be customized with the app). A default color such as green may be provided, although this may be changed with the app. The clock may include a long term (e.g., 5 year life or more) internal recharging battery to store settings even where the clock is not connected to any external power.

The nightlight may have a plurality (e.g., 3 or more) of different brightness options, as well as various other light and color settings, such as low (ultra-low, barely glows in a dark room), medium, high, soft, warm tone, choice of color (amber, blue, purple, green, red, etc.).

The nightlight may stay on for a predetermined time interval (e.g., such as 30 minutes), then shuts off automatically. Length of time that the nightlight stays on can be selectively customized (e.g., in the app, or with controls on the clock itself), e.g., to provide nightlight illumination duration periods of 30 min, 60 min, 2 hours, all night, until the timer goes off, or any period in between.

White Noise: The clock may have a speaker (sound machine) with multiple (e.g., 4) sound options such as static/white noise, waves, rain, lullaby/piano, or the like. Such sound machine noise can be configured to provide white noise or other soothing sounds to facilitate sleep.

Bluetooth: Clock may be able to connect with an associated Pali App running on the adult user's smartphone or the like, where all aspects of the clock may be controlled with the Pali App.

Pali App: May allow the user, e.g., to turn on "hand" clock, hide face, toggle between various face settings, etc. The App may allow the user to set sleep time screen brightness and brightness of screen during countdown, etc.

The App or other controls on the clock may be able to customize the timer schedule to go off at different times on different days (weekend times versus weekday times). Controls may be provided to be able to turn off all clock controls so children can't mess with buttons (e.g., child lock-out function).

Controls may be provided to set clock time, set wake and/or sleep time, set alarm schedules, set sound machine sound selection and duration, set nightlight brightness and duration, set No Reward mode, where storage drawer does not unlock when time set for sleep or nap ends, set unlock reward drawer mode, where drawer can be opened or unlocked at any time when in such mode, set reward override, so the reward drawer cannot open unless an open command is sent from the app. The preceding are merely various examples. Other controls and functions will be apparent to one of skill in the art, in light of the present disclosure. Everything that can be controlled on the clock itself should also be able to be controlled from the App.

Buttons on the clock may be hidden behind a selectively movable or removable panel. Such buttons may include a Set Button, —plus and minus button, —time button, —alarm button, —sound machine button, —sleep/wake button, —Reward button, —Nap time button, etc.

Other features and advantages of the present invention will become apparent from the following detailed description when viewed in conjunction with the accompanying drawings, which set forth particular embodiments of the invention.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
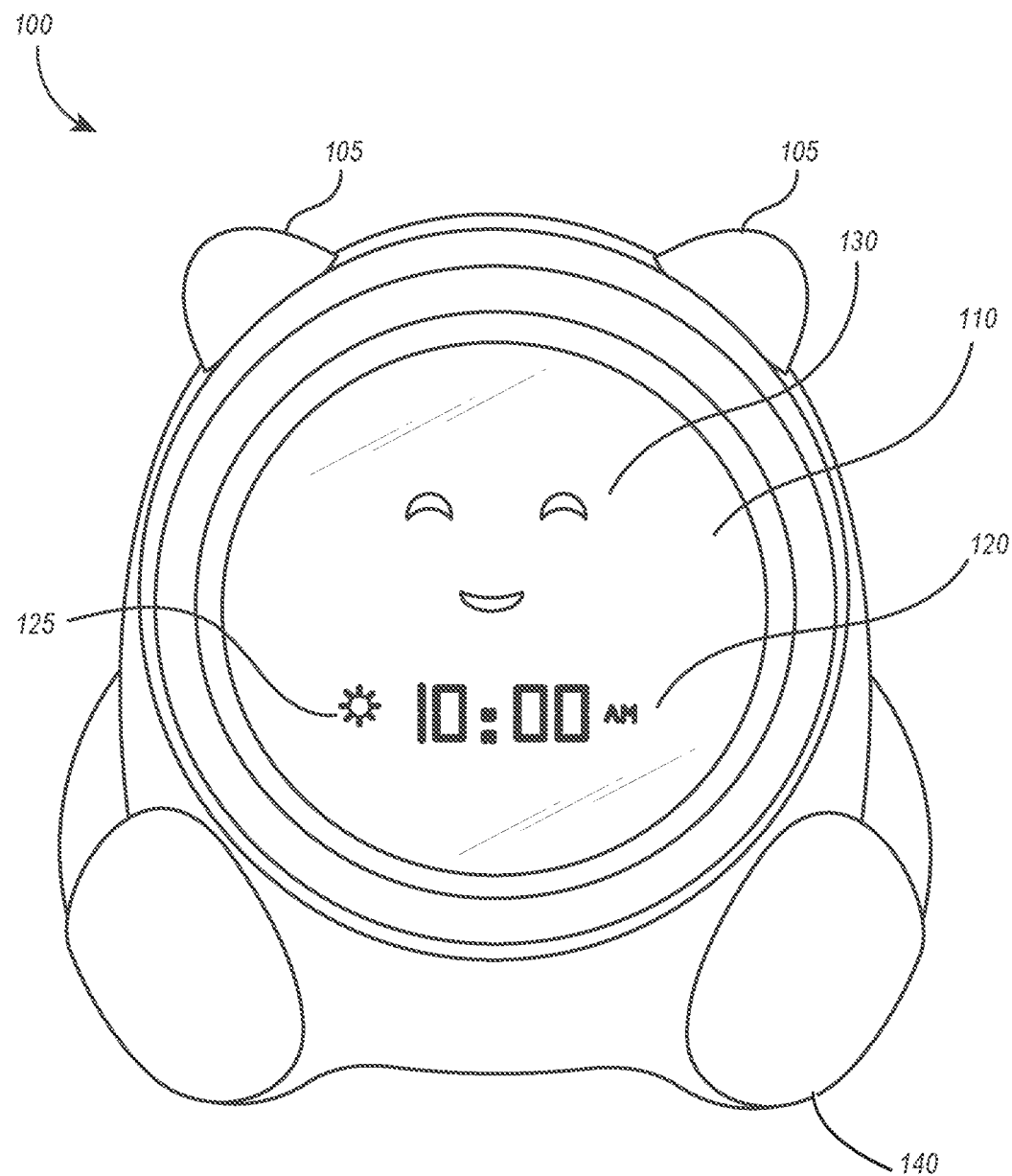
FIG. 1 shows a front view of an exemplary device with the clock face in the "awake" mode.

It is to be understood that this invention is not limited to any particular embodiment described, which may vary. Also, it is to be understood that the terminology used herein is for the purpose of describing particular embodiments only, and is not intended to be limiting, since the scope of this invention will be limited only by the appended claims.

In the following detailed description, numerous specific details are set forth in order to explain and provide a thorough understanding of the present invention. However, it is apparent that the present invention may be practiced without some of these specific details. Thus, all illustrations of the drawings are for the purpose of describing versions of the present invention, and are not intended to limit the scope of the invention.

In the following section, the present invention is described fully by referencing the details in the enclosed drawings, which illustrate certain embodiments of the invention. The numbers shown in this specification refer to the corresponding numbers in the enclosed drawings. The terminology used is to describe the particular embodiment shown and is not intended to limit the scope of the invention. The invention may also be embodied in many other forms in addition to the embodiments shown. Thus, the embodiments shown should not be construed as limiting, but rather, to allow a thorough and complete description of the disclosure that conveys the scope of the invention to a person having ordinary skill in the art in the field of this invention. Therefore, for the terms used herein, the singular forms "the," "a," and "an" are intended to include the plural forms as well as the singular forms, unless the context clearly indicates otherwise. The term "and" includes any and all combinations of one or more of the associated listed items. As used herein, the terms "comprising" and "comprises" when used in this specification, identify specific steps, integers, operations, features, components, and elements, but do not preclude the presence or addition of one or more other steps, operations, features, components, and elements. In addition, the features, components, and elements referenced in the drawings may be exaggerated for clarity.

Unless otherwise defined, all scientific terms, technical terms, or other terms used herein have the same meaning as the term that is understood by one having ordinary skill in the art in the field of this invention. It is also understood that these terms, including their dictionary meaning, should be understood as having the meaning, which is consistent with their definitions in the related relevant art. In addition, the present disclosure is not to be interpreted in an idealized or overly formal sense unless expressly stated so herein. Constructions or functions that are well known in the art may not be fully described in detail for brevity.

In describing the invention, it is understood that a number of steps and methods may be disclosed. Each of these may have individual benefit. Also, each may be used in conjunction with at least one or more of the disclosed steps and methods. Therefore, this description will refrain from stating each and every possible combination of the individual steps and methods for the sake of brevity. Regardless, the specification and related claims should be understood with the combinations that are entirely within the scope of the claims and inventions.

The disclosure in this invention are examples of how it may be implemented and are not intended to limit the scope of the invention to the specific embodiments shown in the accompanying drawings or the description provided herein. The present invention will now be described by example in the following paragraphs by referencing the accompanying drawings, which represent embodiments and alternative embodiments.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

As shown in FIG. 1, the present invention involves a clock designed to help parents sleep longer by helping children know when it is acceptable to get out of bed. The clock 100 may be attractive to children in that its general shape may resemble a stuffed animal with ears, feet 140, arms, and/or a smiling face with open eyes 130 on the clock face 110. Various other shapes and configurations are of course also possible. By "animal shaped", it will be apparent that various configurations suggestive of various living things (e.g., people, animals, etc.) or even fanciful "living" things (e.g., an alien, other anthropomorphic representations, and the like) are within the scope of "animal shaped". Also, as shown in FIG. 1, the clock face 110 is shown as including a digital clock display 120, which displays a symbol for the sun and the letters "AM" to denote morning. The clock face may be comprised of plastic, wood, paper, glass, metal, or any other suitable material.

Figure 2:
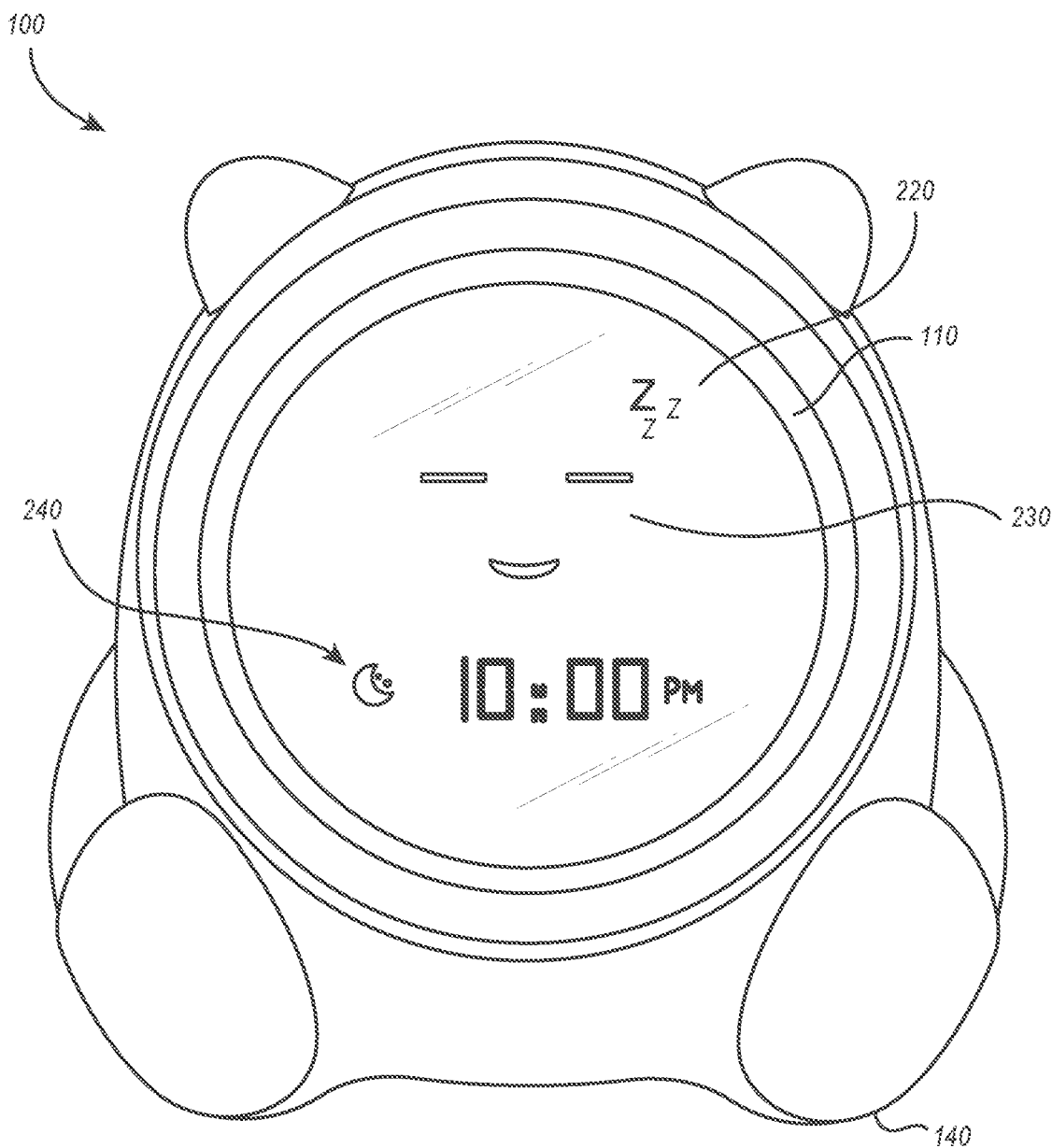
FIG. 2 shows a front view of the device of FIG. 1 with the clock face in the "sleep" mode.

As shown in FIG. 2, the clock face 110 displays a symbol for the moon and stars and the letters "PM" 240 to denote afternoon (e.g., nighttime). Also, as shown in FIG. 2, the clock face 110 displays the letters "ZZZ" 220 and a smiling face with closed eyes 230 to denote sleeping.

Figure 3:
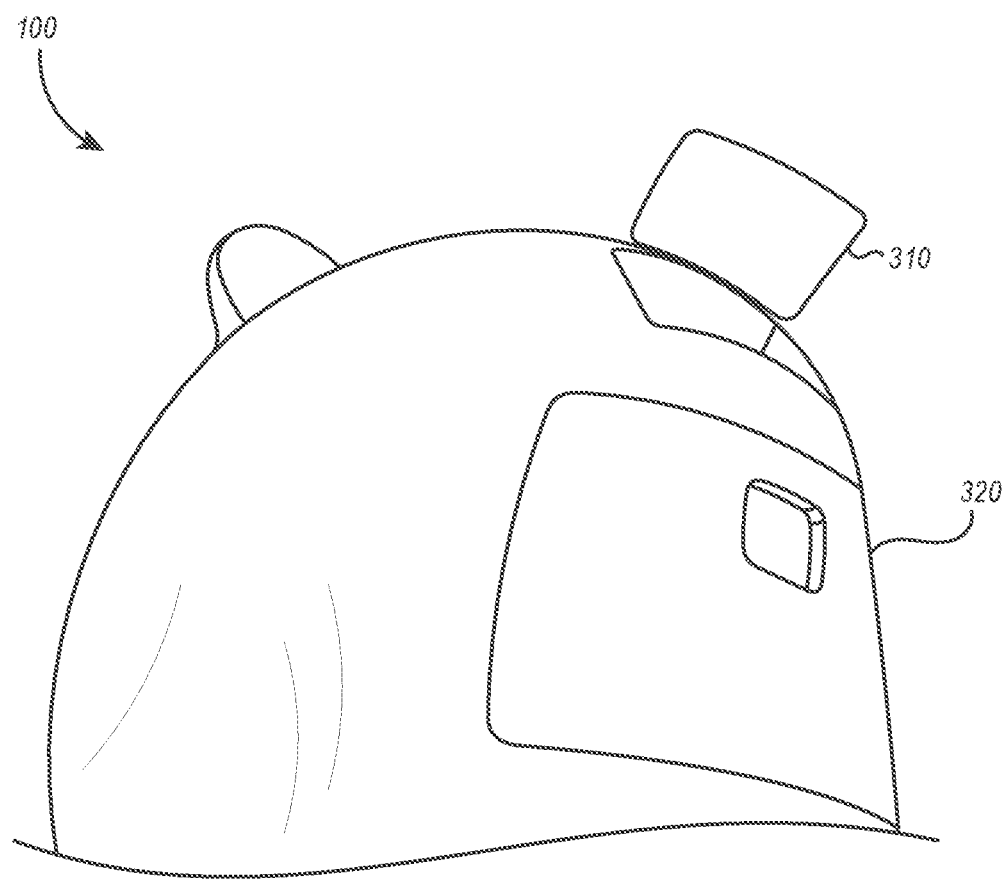
FIG. 3 shows a back side view of the top of the device of FIG. 1.

FIG. 3 is a back side view of the top of the device 100. FIG. 3 shows a button cover 310 to hide programming buttons so that the device maintains a stuffed animal or other "animal shape" look. The programming buttons or a companion app may allow parents to easily customize all features of the clock. FIG. 3 also shows a hidden drawer or compartment 320 in the closed position that may store a reward or trinket for the child, which may open under specific predetermined circumstances dictated by the obedience of the child user. In an embodiment, the reward compartment 320 is not configured as a storage compartment in which is stored a large supply of an item (e.g., candy, a toy or the like), where only a portion of the contents of the compartment are dispensed from such large compartment, at a time, e.g., as is the case in U.S. 2010/0301074 to Koesterich. Rather, the reward compartment 320 may be specifically configured so that the device only includes one such compartment (relatively small) for storage of such a price, within the clock body, where such reward compartment 320 stores the entirety of a prize for the child user (not dispensing a portion of what is stored in a compartment that stores more than what is dispensed to the user in a single instance of dispensing). This allows the child user to retrieve the entire contents of the compartment 320 once the predetermined time set by the adult user has been achieved. The purpose and structure are thus configured to secure and hide the contents of the reward drawer, until such time as the child has earned the price by remaining in their bed or room until the countdown timer reaches zero, rather than a purpose and structure that is configured for rationing dispensing of the contents of a candy or snack container (as in Koesterich).

Figure 4:
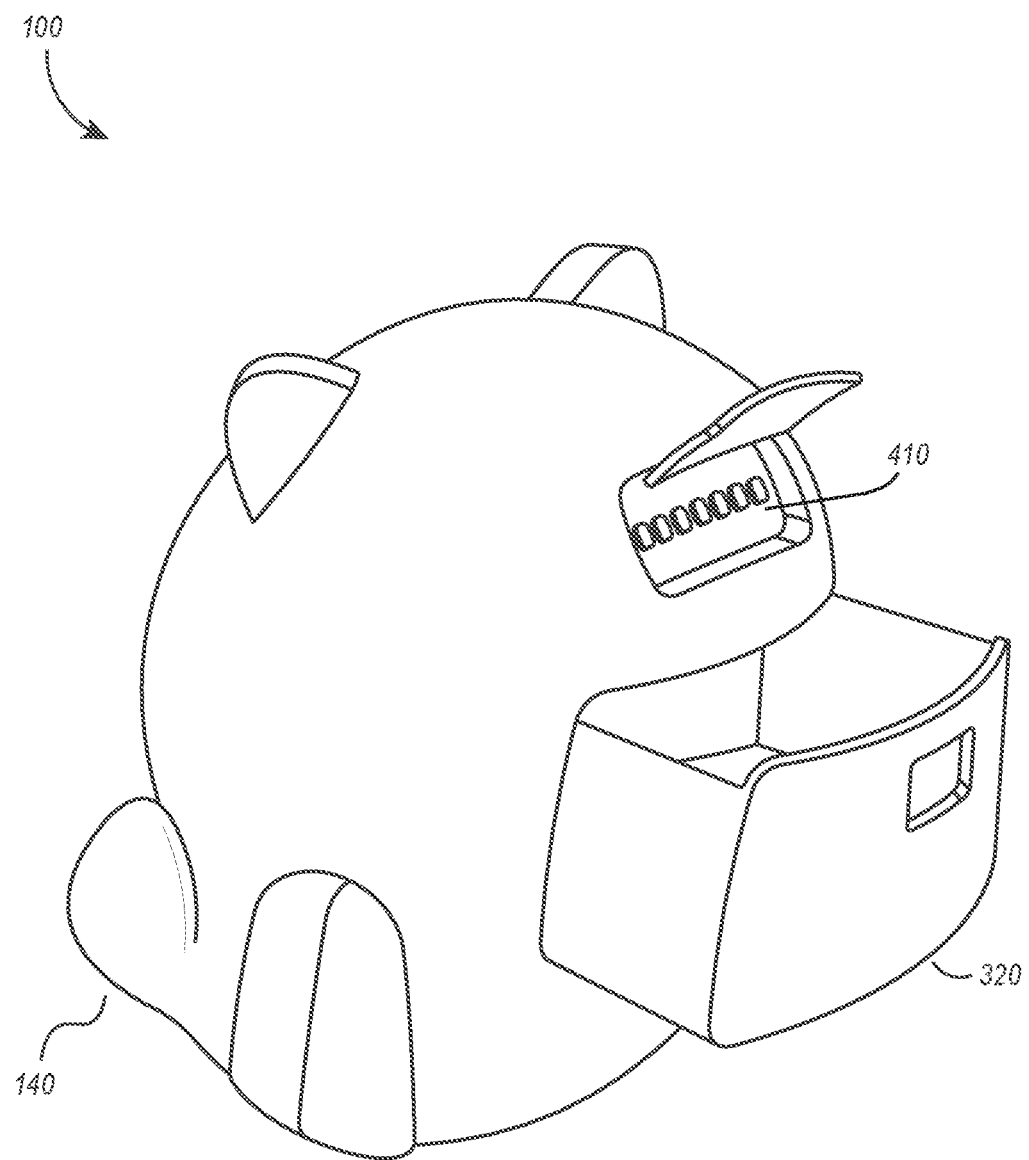
FIG. 4 shows a back side view of the device of FIG. 1.

FIG. 4 is a back side view of the entire device 100. FIG. 4 shows the programming buttons 410 and the drawer or compartment 320 in the unlocked and open position.

Figure 5:
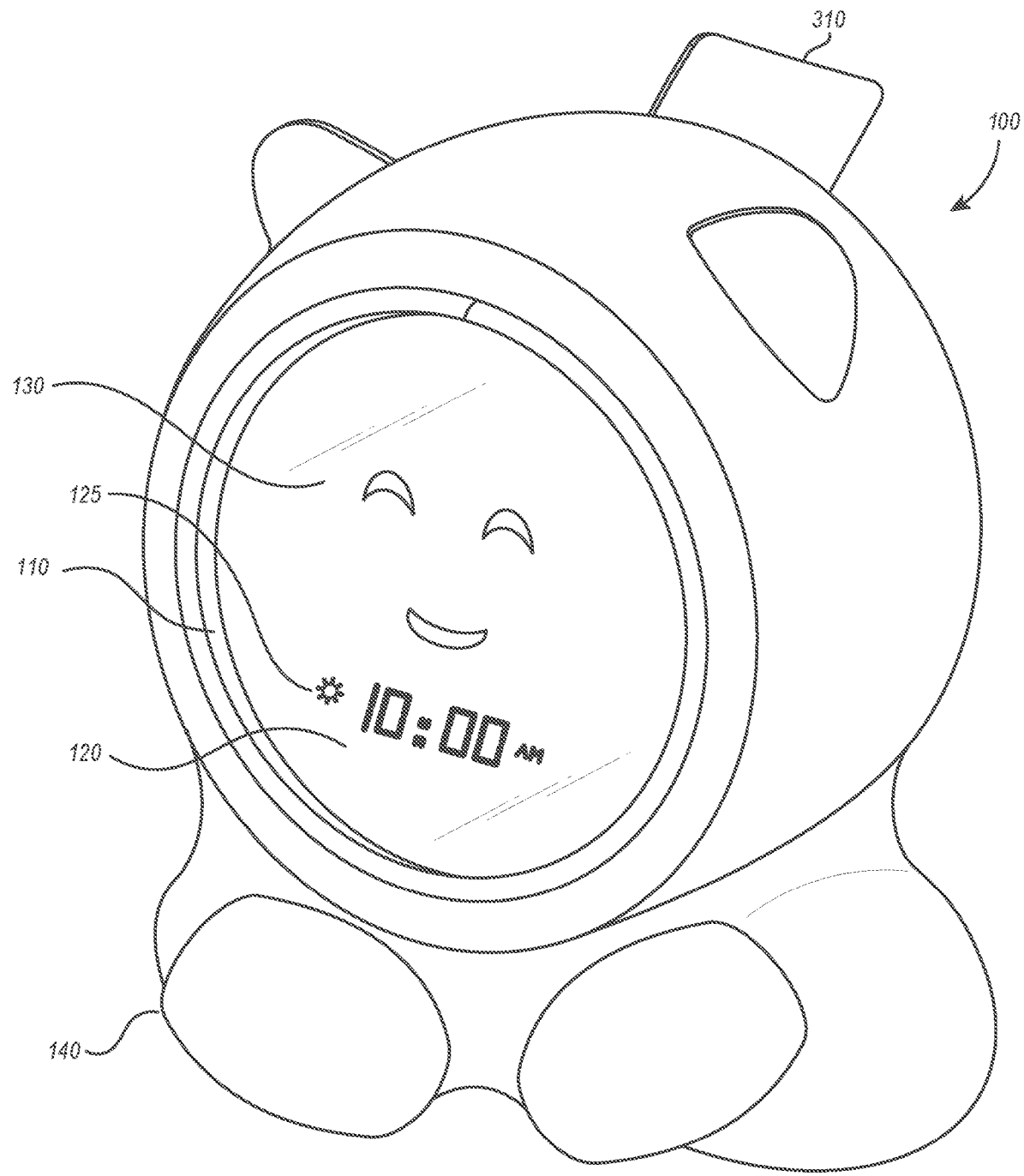
FIG. 5 shows a front side view of the device of FIG. 1 with the clock face in the "awake mode".

FIG. 5 is a drawing of the front side view of the top of the device 100 with the clock face in the awake mode 130. FIG. 5 shows the smiling face with open eyes 130 on the clock face 110, the digital clock display 120 with the sun to denote daytime In this FIG., the button cover 310 is shown in the open position.

Figure 6:
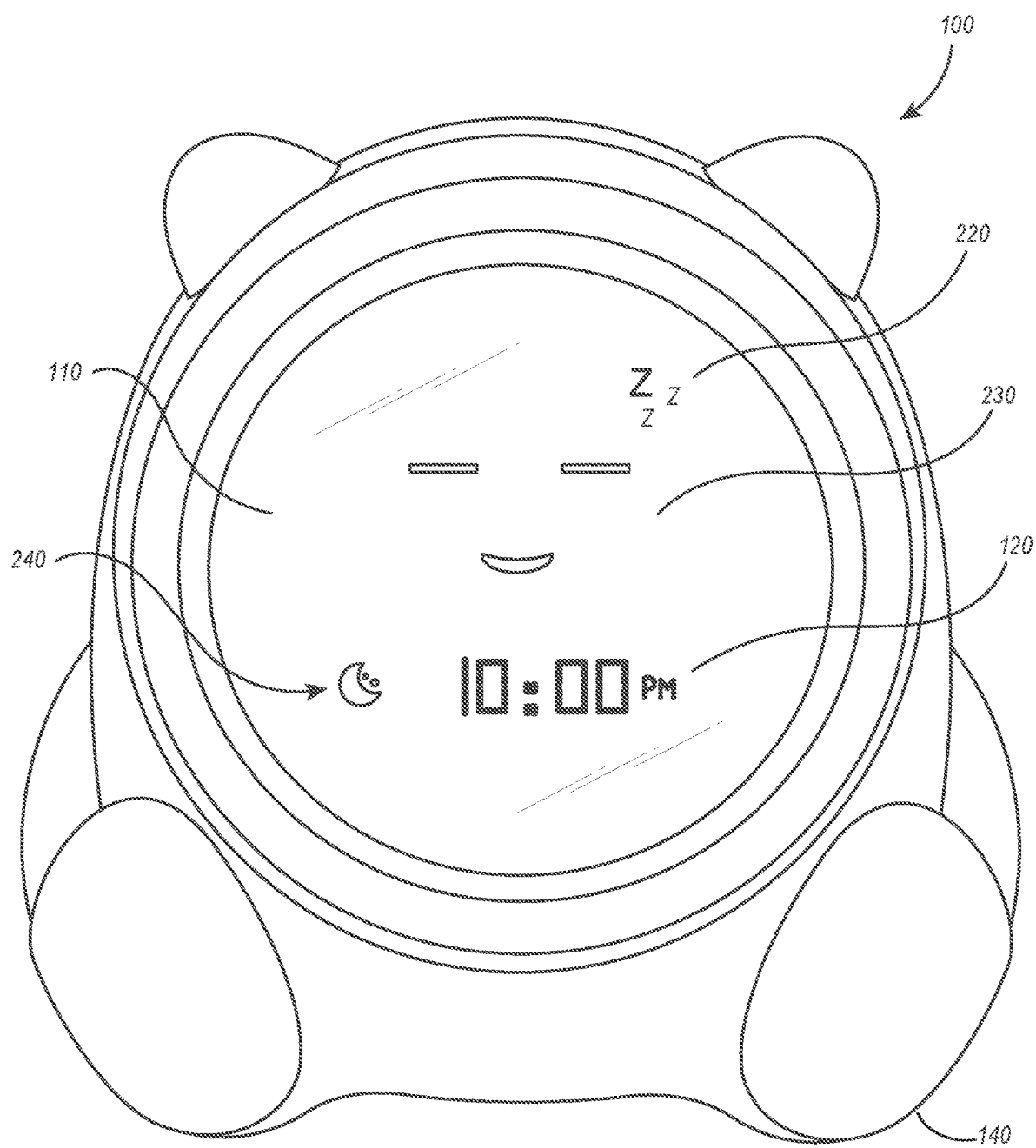
FIG. 6 shows a front view of the device of FIG. 1 with the clock face in the "sleep" mode.

FIG. 6 is a close-up view of the front of the device 100 with the clock face 110 in the sleep mode. Similar to FIG. 2, it shows on the clock face 110 a symbol for the moon and stars 240, denoting nighttime, the letters "ZZZ" 220, and a smiling face 230 with closed eyes to denote that the device is sleeping, and that the child user should be too. Actual cut off times between the nighttime mode (shown in FIG. 6) and the daytime mode (shown in FIG. 5) may be set by the adult user, e.g., using the app. For example, daytime may be set to extend from 7 or 8 am to 7 or 8 pm, or whatever times the adult user wishes to have such transitions set for.

Figure 7:
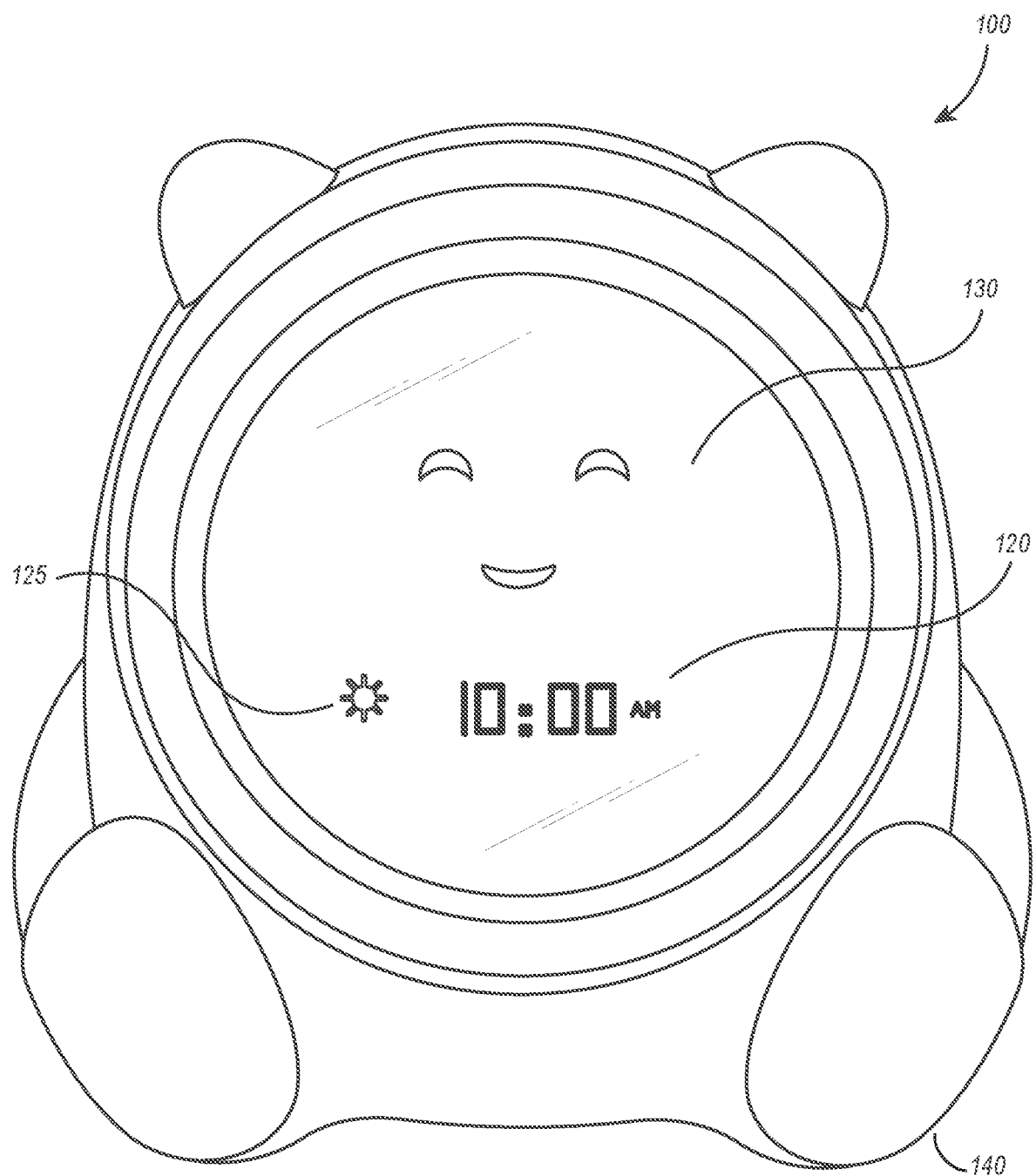
FIG. 7 shows a front view of the device of FIG. 1 with the clock face in the "awake" mode.

FIG. 7 is a close-up view of the front of the device 100 with the clock face 110 in the awake mode. Similar to FIG. 1, it shows a smiling face with open eyes at 130 on the clock face 110 and a digital clock display 120 (showing 10 am), which displays a symbol for the sun to denote daytime.

Figure 8:
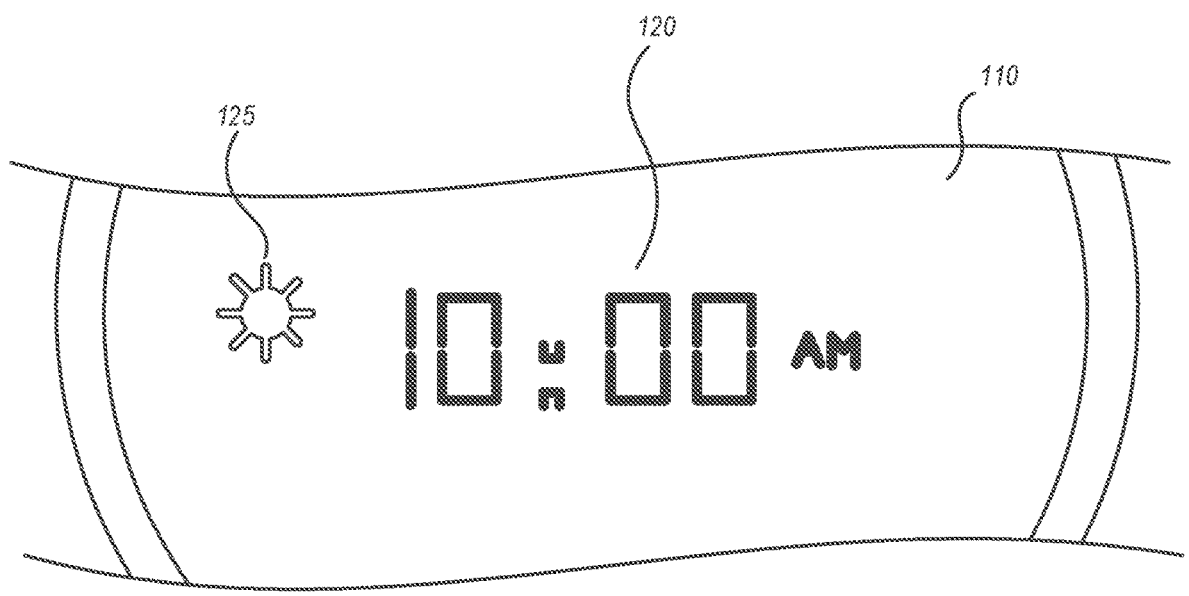
FIG. 8 shows a detailed view of the digital clock mode of the device of FIG. 1.

FIG. 8 is a detailed view showing the digital clock mode of the device showing the digital clock display 120, which displays a symbol for the sun to denote daytime.

Figure 9:
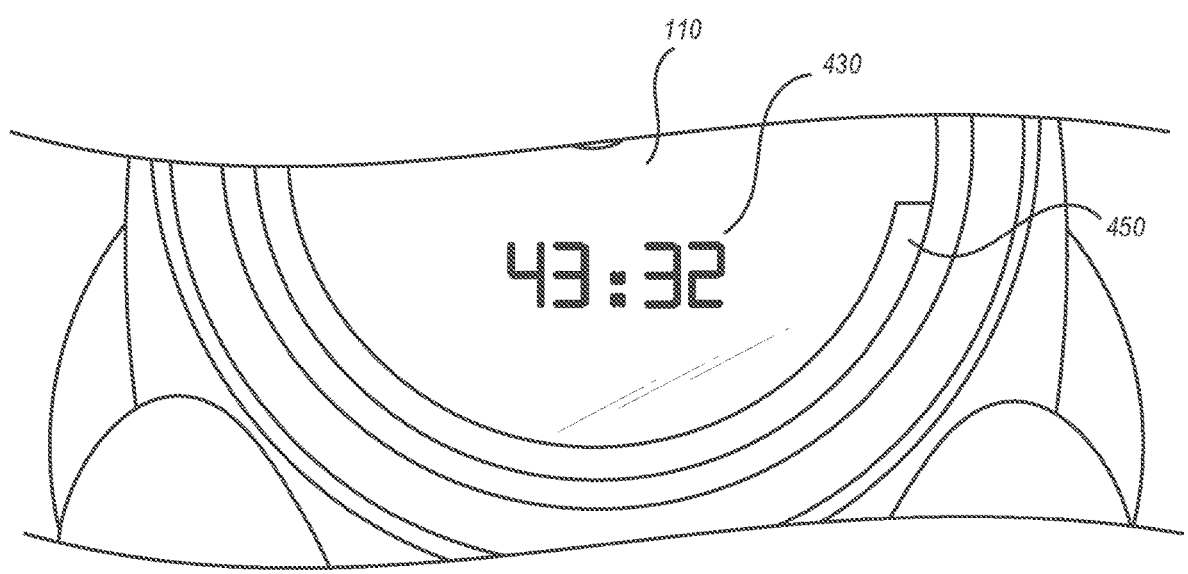
FIG. 9 shows a detailed view of the digital countdown timer mode of the device of FIG.

FIG. 9 is a detailed view showing the digital timer 430 mode of the device, which displays the time remaining for a child to sleep and before the drawer or compartment 320 opens.

Figure 10:
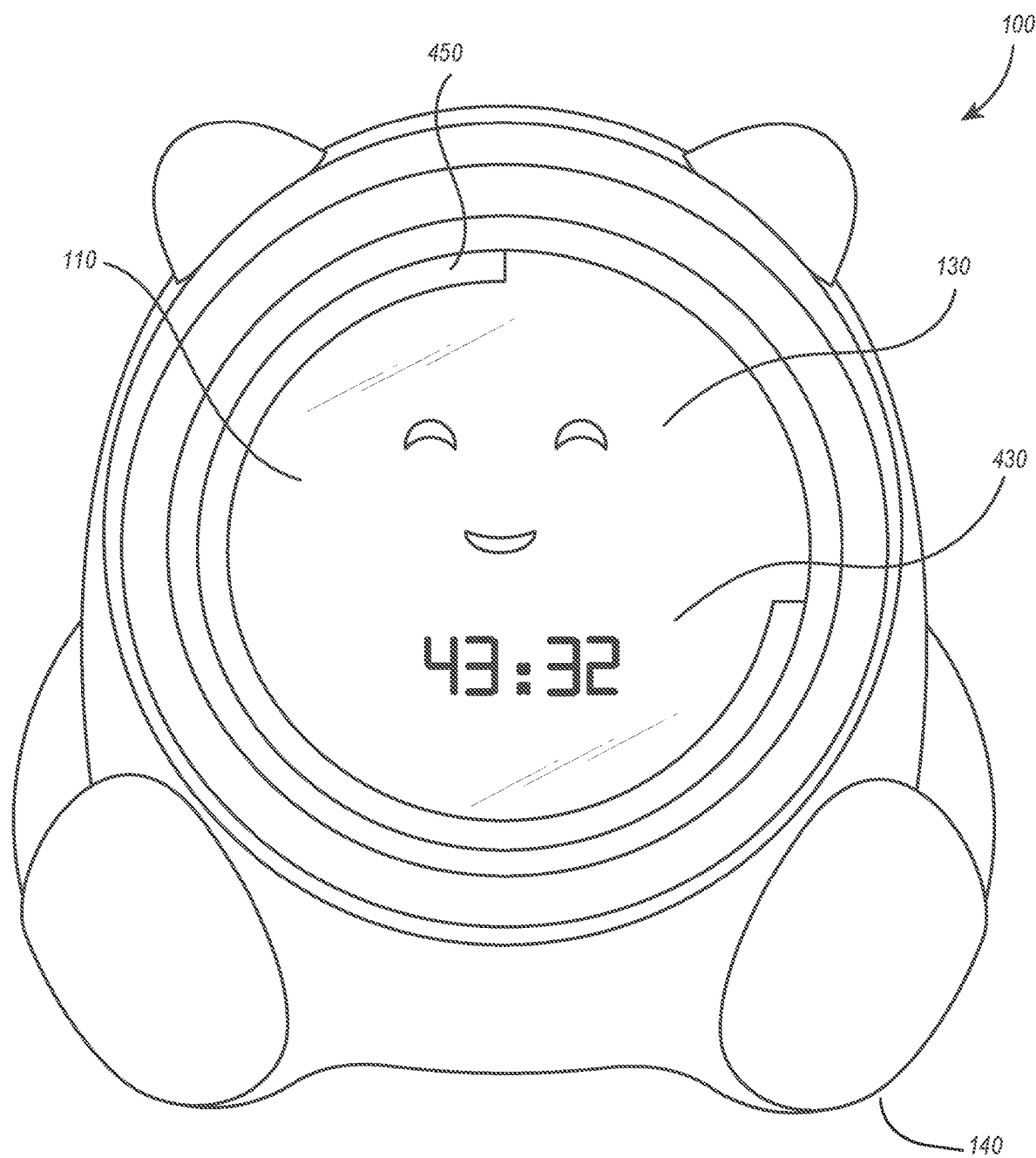
FIG. 10 shows the device of FIG. 1 in the digital countdown timer mode.

FIG. 10 is a detailed view of the digital countdown timer 430 mode of the device. Similar to FIG. 1, it shows a smiling face with open eyes at 130 on the clock face 110. However, rather than a digital clock display 120 showing the time of day, it shows the time remaining for a child to sleep and before the drawer or compartment 320 opens. It will also be noted in FIG. 10 that the perimeter or ring surrounding clock face 110 includes a fraction of the ring or perimeter that is illuminated, but progressively decreasing, corresponding to the time remaining on the digital countdown timer 430.

Figure 11:
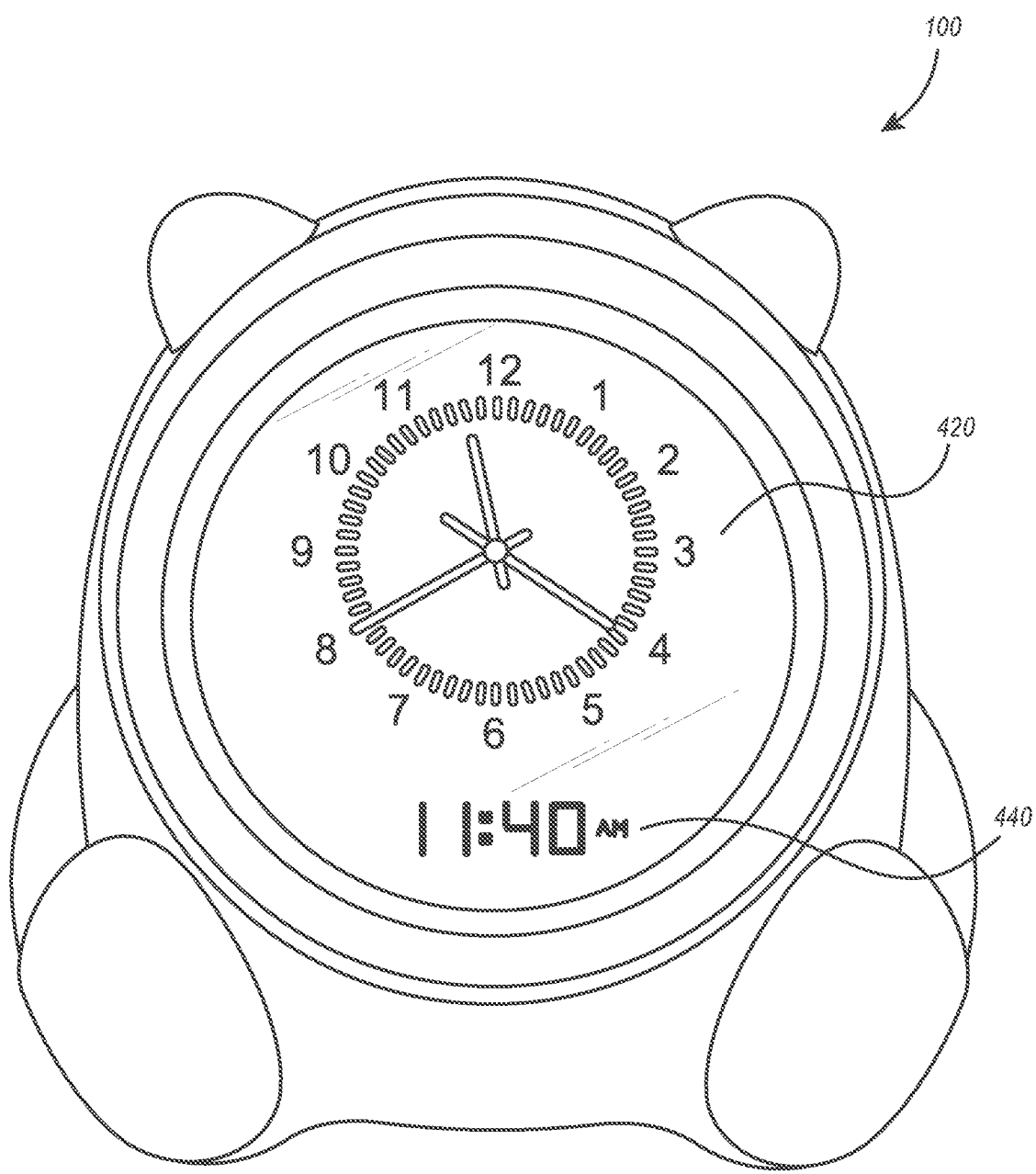
FIG. 11 shows the device of FIG. 1 in the analog "clock hands" timer mode.

FIG. 11 is a detailed view showing the analog "clock hands" mode 420 of the device.

Figure 12:
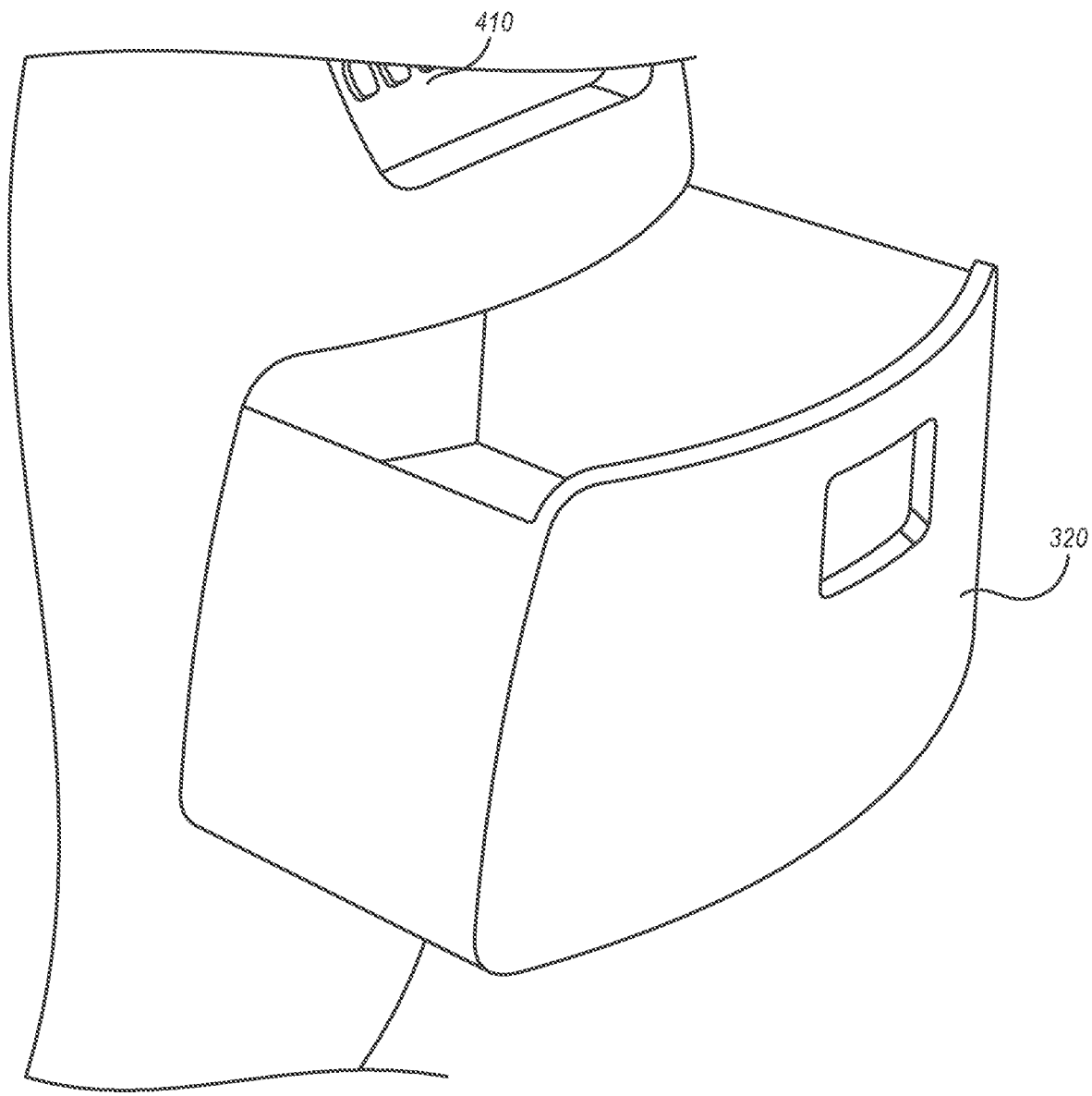
FIG. 12 shows a close-up of the back side view of the device of FIG. 1, with the reward drawer unlocked and open.

FIG. 12 is a close-up view of the back side view of the device 100. Similar to FIG. 4, it shows the programming buttons 410 and the drawer or compartment 320 in the open position.

The present invention provides a reward clock 100 ("Pali Clock") designed to help parents sleep longer by helping children know when it is acceptable to get out of bed. The clock may have a variety of special features, including a display of a digital countdown timer 430 or a visual (circular) "clock hands" type timer 420, a reward function with a drawer or compartment 420, a nightlight, a sound machine, and/or an alarm. The alarm may be an audio alarm, a flashing lamp, strobe lamp, lightbulb, light emitting diode, changes to a display screen, or the like, relative to the clock. A companion app or programming buttons 410 allows parent users of the device to easily customize all features of the clock.

The idea of the Pali clock 100 is that, at a set time, the countdown timer 430 will begin counting down. When the timer 430 ends, the clock lights up and a reward drawer or compartment 420 unlocks. A child can then get a reward for having waited in their room (without bothering his or her parents) until the designated time. At that point, the child may retrieve the reward from compartment 420 and then go find his or her parents. The Pali clock 100 is visually pleasing and simple to use. The exterior may be shaped as shown in the FIGS. It will be apparent that numerous other shapes are possible. The material used for at least certain portions of the clock may be sufficiently transparent to allow an interior light source to show through. A colored ring 450 may be provided around the face 110 of the clock 100. Such a ring 450 may be removable and switchable so that each customer can customize the appearance of their clock to suit their own tastes. The material of such a ring 450 may be formed of a material that is sufficiently transparent to be illuminated from behind, by a light source in the clock face (e.g., LCD, LED or the like), which may progressively decrease the fraction of the lighted perimeter, corresponding to how much time is left when the clock is in the countdown timer mode 430.

A selectively lockable drawer or other compartment 320 may open and close (as shown in FIGS.). The clock may provide buttons 410 for control of various functions that may be hidden by a cover or panel 310. The clock 100 may have buttons 410 to set an alarm, the time, the duration of illumination for a night light, the duration of time for a radio, sound machine, or other audible function to remain on, the sleep or wake time, the duration for a nap time, the brightness of the screen, and/or a Reward or No Reward button. These buttons 410 may be configured in any arrangement, (e.g., in two rows or otherwise arranged), as desired.

The ears 105 may be configured as pushable or otherwise actuable buttons on the exterior of the device. Such ears do not appear to be any control button, so as to again hide the controls. By way of example, the ears 105 of the clock may turn off the alarm or begin nap time. For example, this may be accomplished by holding the appropriate ear for about three seconds to begin nap time. The other ear may be configured to turn on or off the night light or adjust nightlight brightness. The clock body or a designated ear may be touched 3 or more times to access 3 or more levels of brightness (e.g., capacitative or other "touch" controls). The sound machine or radio on the clock may be turned on (or off) by pushing down the ear for 3 seconds or another designated period.

The clock 100 is meant to be a child's nighttime pal that will "sleep" when they sleep and let them know when it is acceptable to wake up and play. The face 110 may be about 2 inches to 12 inches in diameter or other width. The clock face 110 may display eyes and a mouth that can be set by an adult user to "sleep" (as in FIG. 2) and "wake up" (as in FIG. 1) at a specific time. When the countdown timer 430 has begun, the clock face 110 may still display the "sleeping" face symbols, but the ZZZ's 220 may go off.

The digital time (time of day) 120 may be displayed at all times, unless the countdown timer 430 has been activated. When the countdown 430 is active, the time remaining may be shown in place of the time of day (HH:MM or MM: SS, depending on amount of time remaining).

For example, the digital time may show 10:00 AM or the timer 430 may display whatever portion of the nap or sleep time remains (e.g., 43 minutes and 32 seconds as in FIG. 10).

When the visual countdown timer 430 is activated, an illuminated ring 450 around the outside edge of the face may appear. As the countdown proceeds, the lighted portion of ring 450 may recede. For example, the original timer 430 may be one (1) hour long. When the timer 430 is turned on, the full perimeter or circle may be filled. When the timer 430 is down to 45 minutes, there may only be illuminated ¾ a circle, at 30 minutes ½ a circle, etc. In an embodiment, the face 110 may be configured to illuminate such portion of the perimeter, where the portion illuminated constantly and gradually diminishes, providing a visual indication to the child of what fraction of the original time remains at any given point. The user may be provided with different colored rings that can be interchangeably placed over the perimeter face 110 of clock 100, which are back illuminated through the colored ring during use. In another embodiment, user controls may be provided allowing the user to change the color of the illuminated ring, where the display associated with face 110 is a color (e.g., full color) display. An embodiment using interchangeable positionable rings may allow the clock face to be less expensively manufactured to only be monochromatic in color display, but to still provide a desired different color through backlighting.

Illumination of ring 450 progressively diminishes from an initial "full" graphic (e.g., full 360° perimeter ring), so that at any given time the fraction of the illuminated ring 450 corresponds to that fraction of time remaining, that the child user must wait for the prize in the prize drawer. This visual graphical countdown timer is particularly advantageous, as it does not rely on typical number indicia used with timers, which numbers may mean nothing to a young child user, who may not have yet learned how to even count. Such a young user can though appreciate the graphical representation provided by the graphical countdown timer provided by ring 450, which can be seen by the child to continuously and progressively diminish. Such a child user can readily then appreciate their progress towards the predetermined time set by the adult user, when they can leave their bed or room, and the prize in the drawer obtained. Such a diminishing graphical configuration is advantageous as compared to timers that rely on number indicia, or even those which are color coded (e.g., changing colors as the countdown approaches "zero"), as very small children may not understand such numbers, or even colors.

During daytime or the wake time designated by the adult user (e.g., through the App), the sun symbol 125 is illuminated next to the time 120. During the set Sleep Time (also selectively set through the App by the adult user), the moon symbol 240 may be illuminated next to the time.

If selected in the App, during the daytime (wake time), the screen may change from a face (e.g., 130, 230) to an actual clock with hands 420 (FIG. 11), with the digital time 440 displayed below it. The Reward Function is a particularly advantageous aspect of the Pali clock 100. If a child waits until the designated time (e.g., as set by the adult user in the App, or using the Pali clock controls 410), they can retrieve a reward from the reward drawer 320 after it opens once the designated period of time (for nap) or time of day (for waking up in the morning) has passed.

The drawer 320 may be positioned in the back of the clock 100. It will be appreciated that other positioning may also be possible, in other embodiments, e.g., on a side, or on the front, or bottom, although positioning the reward drawer 320 towards the back (i.e., opposite the clock face 110) may be preferred as it places the drawer (even when closed) out of sight from the front. The drawer 320 should be sturdy and slide easily. The dimensions of the drawer 320 may be as desired. In an embodiment, the drawer may be approximately 1 inch to 10 inches wide, 1 inch to 10 inches tall, and 1 inch to 6 inches deep. In a particular embodiment, the drawer may be approximately 3 inches wide, 2 inches tall and 3 inches deep. Any of the dimensions provided herein, such as the above, could be varied by up to 1 inch, by up to 50%, or other amounts, depending on need.

The drawer 320 locks when the Reward/No Reward button (e.g., one of buttons 410) is pushed. This button allows a parent user to push the Reward/No Reward button, e.g., if the child does not stay in their room or bed during nap time, or has gotten up too early in the morning, or the like. For example, the parent may push this button when returning the child to their bed or room. It drawer 320 unlocks when the timer 430 goes off (i.e., counts down to 0) UNLESS the reward/No Reward button has been activated. If that is the case, the drawer 320 remains locked until the timer 430 is reset, and is allowed to countdown again. For example, the Reward/No Reward button may be automatically reset to its default position (which allows the drawer to unlock at the proper time) once the timer runs down to 0. The drawer 320 should preferably lock and unlock silently, with no audible clicking, if possible.

When the timer 430 goes off, the clock face 110 of clock 100 may light up at an intermediate, medium brightness (can be customized with app). The illumination may be in a default color such as green (signaling to the child that it is okay to get up and go find Mom/Dad), although the color may be changed with app. An internal recharging battery may store settings, where the clock is not connected to external power.

The nightlight may have 3 different brightness options→low (ultra-low, barely glows), medium, high, soft, warm tone, choice of color (amber, blue, purple, green, red), etc.

The nightlight may stay on for 30 minutes (or other predetermined period) and then shut off. Length that it stays on can be customized, e.g., 30 min, 60 min, 2 hours, or all night (e.g., until timer 430 counts down to 0). Such a nightlight may be significantly dimmer than typical room lighting (e.g., less than 5 watts, less than 3 watts, less than 2 watts, or less than 1 watt).

White Noise: The clock 100 may have a speaker with multiple (e.g., 4) sound options, such as static/white noise, waves, rain, and/or lullaby/piano.

Bluetooth: Clock 100 may be able to connect with a Pali App running on the adult user's smartphone or the like, and all aspects of the clock may be controlled with the Pali App.

Pali App: May allow the user e.g., to turn on the "hand" clock type display (rather than digital clock display, to show or hide the appropriate face (130, 230), set sleep time, set screen brightness, set brightness of screen during countdown, and any other available settings.

The app or other controls on the clock may be able to customize the timer 430 schedule to go off at different times on different days (weekend times versus weekday times). Controls may be provided to be able to turn off all clock controls so children can't mess with buttons 410.

Controls may be provided to set clock time, set wake and/or sleep time, set alarm schedules, set sound machine sound selection and duration, set nightlight brightness and duration, set No Reward mode, where storage drawer does not unlock when time set for sleep or nap ends, set unlock reward drawer mode, where the drawer can be opened or unlocked at any time when in such mode, set reward override, so the reward drawer cannot open unless an open command is sent from the app. The preceding are merely various examples. Other controls and functions will be apparent to one of skill in the art, in light of the present disclosure. Everything that can be controlled on the clock itself should also be able to be controlled from the App.

Controls may be provided to set clock time, set wake and/or sleep time, set alarm schedules, set sound machine sound and duration, set nightlight brightness and duration, set No Reward mode, where storage drawer does not unlock even though the timer 430 counts down to 0. Controls may be provided to unlock the reward drawer 320, so as to open and/or unlock drawer 320 at any time. Controls may be provided for reward override, so the reward drawer cannot open unless done from the app or other controls. Everything that can be set on the clock should also be able to be set on the app.

In an embodiment, the app and the clock device can be configured to provide two-way voice communication and/or monitoring so that an adult user can speak to and/or monitor the child user remotely through the app (e.g., similar to a baby monitor, but with 2-way voice communication). In an embodiment, the lock may be controllable from such an app, allowing an adult user to selectively lock or unlock the reward compartment.

Buttons 410 may be hidden behind the panel 310. Such buttons may include a plus and minus button, a time button, an alarm button, a sound machine button, a sleep/wake button, the Reward/No Reward button, and/or a nap time button.

While in an embodiment, the visual graphical countdown timer may progressively diminish throughout the entire night, or over another given period which the child user is to stay in their room or bed, in another embodiment, the time duration that the countdown timer is active (as it diminishes) may only be a portion of such time period. In an embodiment, the user (e.g., adult user) has the ability to customize the duration of the graphical countdown timer to achieve such. For example, the last 30 minutes to 2 hours, or 1-2 hours of such a time period may be when a child user is most restless, when the visual graphical countdown timer may be most useful. For example, the user can customize the countdown timer so that the countdown starts 1 hour (or other selected custom duration) before the designated "wake up" time. This way the visual graphical countdown timer diminishes faster (i.e., gets smaller faster) where it only tracks the last hour (rather than an entire 8, 10 or 12 hour night). As a result, the child user is more willing to wait in their room in the morning, as they watch the graphical countdown timer diminish relatively quickly towards zero, when they can get up. Even though the visual graphical countdown timer may not necessarily be active throughout the entire night or nap time, it can, throughout the night or other nap time, give other visual cues, liked closed eyes, etc. to indicate to the child that it is not time to be awake yet.

In an embodiment, when the reward compartment is unlocked, the reward compartment can be manually opened and closed by pulling it with the user's hand.

Although the invention has been explained in relation to various preferred embodiments, it is to be understood that many other possible modifications and variations may be made without departing from the spirit and scope of the invention.

In at least one embodiment, the functions of the device or method described may be implemented in software, firmware, hardware, or any combination thereof. When implemented in software, the functions may be transmitted, as one or more instructions or code on, over or stored on at least one computer-readable medium. The computer-readable media may include both communication media and computer storage media, including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. It should be understood in this disclosure that Bluetooth is an example of wireless communication. The term memory may include volatile or non-volatile (e.g., floppy disks, hard disks, CD-ROMs, flash memory, read-only memory (ROM), and random access memory (RAM)).

The method may comprises receiving data over a cellular, wireless, satellite, or other network to a special purpose computer with a non-transitory computer readable medium. In one or more of the embodiments, the functions described herein may be implemented in any combination of hardware, software, firmware, etc. The functions may be stored or transmitted as one or more software instructions, computer-executable instructions, or processor-executable instructions, or code on a tangible non-transitory computer readable medium or on a non-transitory processor-readable storage medium, if implemented in software. The steps of an algorithm, process, or method disclosed herein may be embodied in a processor-executable software module that may reside on a non-transitory computer readable medium. Non-transitory computer readable medium readable media includes both computer storage media and communication media including any medium that facilitates transfer of a computer program from one place to another. A non-transitory storage media may be any available media that may be accessed by the special purpose host computer system.

Also, combinations of the above should be included within the scope of non-transitory computer readable medium. In addition, the operations of an algorithm, process, or method may reside as one or any combination or codes, set of codes, instructions, or sets of instructions on a non-transitory machine readable medium, which may be incorporated into a computer program product.

By way of an example, and not as a limitation, a non-transitory computer readable medium may comprise Random-Access Memory (RAM), Read-Only Memory (ROM), Programmable Read-Only Memory (PROM), Erasable Programmable Read-Only Memory (EPROM), Electrically Erasable Programmable Read-Only Memory (EEPROM), Compact Disc Read-Only Memory (CD-ROM) or other optical disk storage, magnetic disk storage, or other optical or magnetic storage devices, or any other medium that may be used to store program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically or optically with lasers.

Also, combinations of the above should be included within the scope of non-transitory computer readable medium. In addition, the operations of an algorithm, process, or method may reside as one or any combination or codes, set of codes, instructions, or sets of instructions on a non-transitory machine readable medium or an a non-transitory computer readable medium, which may be incorporated into a computer program product. All illustrations of the drawings are for the purpose of describing selected versions of the present invention and are not intended to limit the scope of the present invention.

The invention claimed is:

1. A clock device for training a child user to remain in their bed or room until a predetermined time, the clock device comprising:
   a clock body in a shape of an animal body, comprising at least one of an analog or digital clock display on the animal shaped clock body;
   the clock body including a clock face that is configured to display a visual graphical countdown timer corresponding to how much time the child user is to remain in their bed or room;
   wherein the visual graphical countdown timer begins as one or more graphics, which progressively diminish or go away as the countdown timer progressively counts down towards the predetermined time, at which zero time remains, and at which time the one or more graphics have diminished to zero or gone away; and
   a light on or within the clock body, wherein the light automatically illuminates when the visual graphical countdown timer diminishes to zero or goes away.

2. The device of claim 1, wherein the clock body in the shape of an animal body includes at least one of feet, ears, or arms.

3. The device of claim 1, wherein the clock device further comprises a sound machine configured to provide white noise or other soothing sounds to facilitate sleep.

4. A clock device for training a child user to remain in their bed or room until a predetermined time, the clock device comprising:
   a clock body including a clock face that is configured to display a visual graphical countdown timer corresponding to how much time the child user is to remain in their bed or room;
   wherein the visual graphical countdown timer begins as one or more graphics, which progressively diminish as the countdown timer progressively counts down towards the predetermined time, at which zero time remains, and at which time the progressively diminishing one or more graphics has diminished to zero; and
   a light on or within the clock body, wherein the light automatically illuminates when the visual graphical countdown timer diminishes to zero;
   wherein a time duration provided by the visual graphical countdown timer is customizable by user.

5. The device of claim 4, wherein the visual graphical countdown timer is customizable such that the visual graphical countdown timer can be made to start counting down for the last 30 minutes to 2 hours of a night that the child user is to remain in their room or bed.

6. The device of claim 4, wherein the visual graphical countdown timer is customizable such that the visual graphical countdown timer can be made to start counting down for an entire night.

7. The device of claim 4, wherein the clock body is in the shape of an animal body.

8. The device of claim 7, wherein the clock body in the shape of an animal body includes at least one of feet, ears, or arms.

9. The device of claim 4, wherein the clock device further comprises a sound machine configured to provide white noise or other soothing sounds to facilitate sleep.

10. A clock device system for training a child user to remain in their bed or room until a predetermined time, the clock device system comprising:
    a clock device comprising:
    a clock body including a clock face that is configured to display a visual graphical countdown timer corresponding to how much time the child user is to remain in their bed or room;
    wherein the visual graphical countdown timer begins as one or more graphics, which progressively diminish as the countdown timer progressively counts down towards the predetermined time, at which zero time remains, and at which time the progressively diminishing one or more graphics has diminished to zero; and
    a light on or within the clock body, wherein the light automatically illuminates when the visual graphical countdown timer diminishes to zero; and
    an app configured to run on an adult user's smartphone, tablet, or other mobile device, wherein the app is configured to control the clock device.

11. The system of claim 10, wherein the app and the clock device are configured to provide two-way voice communication and/or monitoring so that an adult user can speak to and/or monitor the child user remotely through the app.

12. The system of claim 10, wherein the clock body is in the shape of an animal body.

13. The system of claim 12, wherein the clock body in the shape of an animal body includes at least one of feet, ears, or arms.

14. The system of claim 10, wherein the clock device further comprises a sound machine configured to provide white noise or other soothing sounds to facilitate sleep.

15. A clock device for use by an adult user or a child user, for providing a reward to the child user after a predetermined time, the clock device comprising:
    a clock body comprising at least one of an analog or digital clock display on the clock body;
    one or more reward compartments provided on or within the clock body, the reward compartment storing a reward for the child user;
    a lock in or on the clock body, in communication with the reward compartment, the lock maintaining the reward compartment in a locked configuration until the predetermined time set by the user or is overridden;
    wherein the reward compartment comprises the lock in communication with a timer, the timer being electronically or mechanically coupled to the lock such that the reward compartment remains locked until the predetermined time set by the adult user has been achieved, so that the reward may be retrieved by the child user at the predetermined time.

16. The device of claim 15, wherein the lock is controllable from an app configured to run on an adult user's smartphone, tablet, or other mobile device, to allow an adult user to selectively lock or unlock the reward compartment.

17. The device of claim 15, wherein when the reward compartment is unlocked, the reward compartment can be manually opened and closed by pulling.

18. The device of claim 15, wherein the clock body is in the shape of an animal body.

19. The device of claim 18, wherein the clock body in the shape of an animal body includes at least one of feet, ears, or arms.

20. The device of claim 15, wherein the clock device further comprises a sound machine configured to provide white noise or other soothing sounds to facilitate sleep.

* * * * *